US011786622B2

(12) United States Patent
Godfroy et al.

(10) Patent No.: US 11,786,622 B2
(45) Date of Patent: Oct. 17, 2023

(54) FAR UV-C LIGHT APPARATUS

(71) Applicants: Thomas J. Godfroy, Huntsville, AL (US); Robert V. Albertson, Mound, MN (US)

(72) Inventors: Thomas J. Godfroy, Huntsville, AL (US); Robert V. Albertson, Mound, MN (US)

(73) Assignee: ULTRA-VIOLET SOLUTIONS, LLC, Huntsville, AL (US)

(*) Notice: Subject to any disclaimer, the term of this patent is extended or adjusted under 35 U.S.C. 154(b) by 344 days.

(21) Appl. No.: 17/313,615

(22) Filed: May 6, 2021

(65) Prior Publication Data

US 2021/0346560 A1 Nov. 11, 2021

Related U.S. Application Data

(60) Provisional application No. 63/022,143, filed on May 8, 2020.

(51) Int. Cl.
*A61L 2/10* (2006.01)
*A61L 2/26* (2006.01)
*A61L 2/00* (2006.01)

(52) U.S. Cl.
CPC .............. *A61L 2/26* (2013.01); *A61L 2/0047* (2013.01); *A61L 2/10* (2013.01); *A61L 2202/11* (2013.01); *A61L 2202/14* (2013.01); *A61L 2202/16* (2013.01)

(58) Field of Classification Search
CPC ...... A61L 2/10; A61L 2/26; A61L 2/28; A61L 2/0047; A61L 2202/11; A61L 2202/14; A61L 2202/16; A61L 2202/17; A61L 2202/20

See application file for complete search history.

(56) References Cited

U.S. PATENT DOCUMENTS

| | | | |
|---|---|---|---|
| 3,657,590 A | 4/1972 | Johnson | |
| 3,771,007 A | 11/1973 | Johnson | |
| 3,906,236 A * | 9/1975 | Callahan | A61L 2/10 250/455.11 |
| 4,710,634 A * | 12/1987 | Brookes | A61L 2/10 16/904 |
| 4,786,812 A * | 11/1988 | Humphreys | A61L 9/20 250/455.11 |
| 4,952,369 A | 8/1990 | Belilas | |
| 5,459,944 A * | 10/1995 | Tatsutani | A47K 10/48 34/202 |
| 5,575,537 A | 11/1996 | Huang et al. | |
| 5,920,075 A * | 7/1999 | Whitehead | A61L 2/10 250/492.1 |
| 6,005,254 A * | 12/1999 | Wijtsma | A61N 5/0614 250/493.1 |
| 6,242,753 B1 * | 6/2001 | Sakurai | A61L 2/10 250/493.1 |

(Continued)

*Primary Examiner* — Sean M Luck
(74) *Attorney, Agent, or Firm* — R. John Bartz

(57) ABSTRACT

A Far UV-C light apparatus has a Far UV-C lamp located within a housing emitting a Far UV-C light having a wavelength of 222±1 nm for destroying pathogens. A quarter wave generator supplies electric energy to the Far UV-C lamp. A handle connected to the housing allows the Far UV-C device to be hand held and moved to a selected location.

20 Claims, 8 Drawing Sheets

(56) References Cited

U.S. PATENT DOCUMENTS

| | | | |
|---|---|---|---|
| 6,431,189 B1* | 8/2002 | Deibert | A61L 2/24 604/289 |
| 6,579,495 B1 | 6/2003 | Maiden | |
| 6,730,113 B2* | 5/2004 | Eckhardt | A61N 5/0624 604/20 |
| 6,826,848 B1* | 12/2004 | Delaney | A45D 29/00 34/90 |
| 6,971,939 B2 | 12/2005 | Claus et al. | |
| 7,148,497 B2 | 12/2006 | Gardner | |
| 7,626,187 B2 | 12/2009 | Youts | |
| 7,714,511 B2 | 5/2010 | Mizojibi et al. | |
| 7,834,335 B2 | 11/2010 | Harmon | |
| 7,859,191 B2 | 12/2010 | Matsuzawa et al. | |
| 7,918,229 B2 | 4/2011 | Cumble et al. | |
| 7,989,779 B1* | 8/2011 | Ray | A61L 2/10 250/493.1 |
| 8,130,099 B2 | 3/2012 | Steinel | |
| 8,164,239 B2 | 4/2012 | Fujisawa et al. | |
| 8,337,770 B2* | 12/2012 | Wind | A61L 2/10 250/455.11 |
| 8,398,264 B2 | 3/2013 | Anderson et al. | |
| 8,481,985 B2 | 7/2013 | Neister | |
| 8,506,103 B2 | 8/2013 | Limura et al. | |
| 8,558,203 B1 | 10/2013 | Gardner | |
| 8,753,575 B2 | 6/2014 | Neister | |
| 8,865,264 B2 | 10/2014 | Haack et al. | |
| 8,946,662 B2 | 2/2015 | Cooper et al. | |
| 8,975,605 B2 | 3/2015 | Neister | |
| 9,039,966 B2 | 5/2015 | Anderson et al. | |
| 9,095,633 B1* | 8/2015 | Dayton | A61L 2/10 |
| 9,603,956 B2 | 3/2017 | Newham | |
| 9,649,398 B1* | 5/2017 | York | E05B 1/0069 |
| 9,651,117 B2 | 5/2017 | Pringle et al. | |
| 9,687,575 B2* | 6/2017 | Farren | A61L 2/10 |
| 9,867,894 B2* | 1/2018 | Stibich | A61L 9/18 |
| 9,993,571 B2 | 6/2018 | Lin et al. | |
| 10,092,669 B2* | 10/2018 | Marshall | A61L 2/08 |
| 10,174,424 B2 | 1/2019 | Tawares et al. | |
| 10,245,341 B2* | 4/2019 | Stibich | A23L 3/28 |
| 10,376,605 B1 | 8/2019 | Majdall et al. | |
| 10,755,901 B2 | 8/2020 | Chambers et al. | |
| 2003/0197026 A1* | 10/2003 | Ashe | B65F 1/06 222/174 |
| 2003/0197122 A1* | 10/2003 | Faiola | G01N 21/94 250/461.1 |
| 2004/0056201 A1* | 3/2004 | Fink | A61L 2/202 250/352 |
| 2004/0175290 A1* | 9/2004 | Scheir | A61L 2/10 422/1 |
| 2004/0249369 A1* | 12/2004 | Muzzi | A61N 5/0616 606/9 |
| 2004/0263043 A1 | 12/2004 | Claus et al. | |
| 2006/0171843 A1* | 8/2006 | Spears | A61L 2/24 422/292 |
| 2007/0045641 A1 | 3/2007 | Chna et al. | |
| 2007/0222554 A1* | 9/2007 | Hart | G07C 9/25 340/5.6 |
| 2008/0061667 A1 | 3/2008 | Gartner et al. | |
| 2008/0192458 A1* | 8/2008 | Li | G02B 6/005 313/498 |
| 2008/0258601 A1 | 10/2008 | Witten et al. | |
| 2009/0143842 A1* | 6/2009 | Cumbie | A61N 5/0624 600/365 |
| 2009/0314308 A1* | 12/2009 | Kim | A61L 2/0088 134/1 |
| 2010/0032589 A1* | 2/2010 | Leben | A61L 2/10 250/504 R |
| 2010/0084486 A1* | 4/2010 | Kim | A61L 2/22 239/71 |
| 2010/0134296 A1* | 6/2010 | Hwang | G08B 21/245 340/573.1 |
| 2011/0156581 A1 | 6/2011 | Yasuda | |
| 2011/0174992 A1* | 7/2011 | Sakita | A61L 2/10 250/492.1 |
| 2012/0187146 A1* | 7/2012 | Chopra | A61L 2/16 222/23 |
| 2012/0305804 A1* | 12/2012 | Goldman | E05B 1/0069 250/492.1 |
| 2015/0265346 A9 | 9/2015 | Pehrson et al. | |
| 2016/0030766 A1* | 2/2016 | Scritchfield | G06V 40/107 607/91 |
| 2016/0225604 A1 | 8/2016 | Imamura | |
| 2016/0296649 A1* | 10/2016 | Ramanand | A61L 2/10 |
| 2016/0339133 A1 | 11/2016 | Lichtblau | |
| 2017/0080117 A1* | 3/2017 | Gordon | A61L 2/084 |
| 2017/0173200 A1* | 6/2017 | Wyman | A47K 5/1217 |
| 2017/0290934 A1* | 10/2017 | Dobrinsky | G02B 19/0095 |
| 2017/0318964 A1* | 11/2017 | McKnight | A61L 2/22 |
| 2018/0214588 A1* | 8/2018 | Casares | A61L 2/202 |
| 2018/0221521 A1* | 8/2018 | Shur | A61L 2/00 |
| 2018/0243458 A1* | 8/2018 | Shatalov | A61L 9/20 |
| 2018/0339075 A1* | 11/2018 | Kennedy | A61L 2/24 |
| 2019/0070326 A1* | 3/2019 | Xie | A61L 2/26 |
| 2019/0172336 A1* | 6/2019 | Haidegger | G08B 21/245 |
| 2019/0255201 A1* | 8/2019 | Rosen | A61L 2/0052 |
| 2019/0262487 A1* | 8/2019 | Gil | A61L 2/202 |
| 2019/0321499 A1* | 10/2019 | Igarashi | A47K 10/48 |
| 2020/0050040 A1 | 5/2020 | Gross et al. | |
| 2020/0215210 A1 | 7/2020 | Rosen et al. | |
| 2020/0330638 A1 | 10/2020 | Hsu-Luk et al. | |

\* cited by examiner

FAR UV-C LIGHT APPARATUS

CROSS REFERENCE TO RELATED APPLICATION

This application claims the priority of U.S. Provisional Patent Application Ser. No. 63/022,143 filed May 8, 2020.

FIELD OF THE INVENTION

The invention relates to Far UV-C light devices for eradicating and destroying pathogens on surfaces, objects and the epidermis of a human.

BACKGROUND OF THE INVENTION

Germicidal ultraviolet light with a wavelength of 254 nanometers (254 nm) is a long time standard for germicidal light fixtures. The germicidal light is identified as Far UV-C light that is emitted from a Far UV-C light source, such as a lamp or light emitting diodes. The Far UV-C light sterilizes environments by eradicating and neutralizing pathogens including viruses, bacteria, spores, and yeasts. Portable UV-C wands and stationary products have UV-C light lamps that emit UV-C light to destroy or neutralize pathogens. Examples of germicidal UV-C light devices and UV-C lamps are disclosed in the following U.S. patents and U.S. patent application publications.

U.S. Pat. No. 4,952,369 discloses a hand held ultra-violet flashlight for sterilizing objects and surfaces. An ultra-violet lamp enclosed in a housing is connected to batteries operable to activate the lamp to generate ultra-violet light in sufficient intensity to disinfect objects at relatively short distances. A handle is extended from the housing for hand holding the portable flashlight.

U.S. Pat. No. 6,971,939 discloses a method of making an excimer lamp having a glass cylindrical tube surrounding a chamber for a gas. A first cylindrical inner electrode is deposed on the inside surface of the tube. A second electrode is on the outside cylindrical surface of the tube. At least one of the electrodes can be in the shape of a mesh or grid. The electrodes are described as "aluminum or the like." The electrodes are deposed on the lamp surfaces by deposition techniques including chemical vapor deposition, physical vapor deposition, screen printing and sputtering. A photolithography process that etches the mesh on the surface of the lamp can also be used. A protective layer covers the electrodes to prevent oxidation of the electrodes during lamp operation. The method includes covering the electrode with a protective layer that separates the electrodes from the environment adjacent to the excimer lamp.

U.S. Pat. No. 7,714,511 discloses an excimer lamp having a vessel. A wire mesh electrode is arranged on the top surface of the vessel. A second wire mesh electrode is on the bottom surface of the vessel. The electrodes are formed by vacuum evaporation.

U.S. Pat. No. 7,834,335 discloses a hand held sterilization device having a cover housing accommodating a light housing and a battery. The cover housing serves as a handle for holding and moving the device across a target surface to sterilize or disinfect the surface. A UV-C light source on the light housing comprises a UV-C lamp or light emitting diodes that emit UV-C light at about 240 nm to 290 nm that destroys microorganisms.

U.S. Pat. No. 7,859,191 discloses a silica glass vessel filled with xenon gas. Electrodes are on opposite sides of the vessel. The electrodes are formed by paste-coating the vessel with metallic electrode material or by means of circuit printing operations.

U.S. Patent Application Publication No. 2011/0156581 discloses a quartz glass lamp. Electrodes are metal plates fixed tightly to opposite outer surfaces of the lamp. A mixture of krypton and chlorine gas fills the discharge chamber. An excimer light having the wavelength of 222 nm is emitted.

U.S. Patent Application Publication No. 2016/0225604 discloses an excimer lamp comprising a quartz glass tube. A coiled inner tungsten electrode is located axially within the tube chamber. A net-like outer electrode is located on the outer surface of the tube. The outer electrode is a plurality of wires fixed to the tube. A rare gas, such as xenon gas, argon gas or krypton gas, is within the tube.

U.S. Patent Application Publication No. 2020/0215210 discloses a Far UV-C light device for eliminating pathogens on localized areas and air surrounding a surface. The device includes a hand grip for holding and moving the device relative to a surface. The device has a Far UV-C light source with a wavelength between 200 nm and 230 nm. The light source includes an excimer lamp or light emitting diodes that emits illumination having a wavelength of 222 nm. Rechargeable batteries are utilized to energize the light source.

SUMMARY OF THE INVENTION

The UV-C light apparatus of the invention utilizes Far UV-C light to sanitize surfaces and objects by subjecting the surfaces and objects to Far UV-C light. The Far UV-C light device is stationary or portable and utilized to sanitize selected surfaces, air surrounding the surfaces and objects on the surfaces. The UV-C light apparatus has a light wavelength that is safe for humans while eliminating pathogens. The Far UV-C light apparatus has a Far UV-C light source located within a housing. The Far UV-C light source emits UV-C light having a light wavelength or spectrum of between 200 nm and 230 nm. The optimum UV-C light wavelength is 222±1 nm to effectively destroy or neutralize pathogens including viruses, bacteria and microorganisms.

In one embodiment of the UV-C light apparatus, a handle connected to the housing supports a battery operable to supply electric energy to activate the Far UV-C light source. An electric circuit transmits electric energy from the battery to the Far UV-C light source. The electric circuit includes a transformer operable to provide a voltage to the Far UV-C light source to activate the Far UV-C light source to emit Far UV-C light. The electric circuit can also include a motion sensor operable to activate the UV-C light source for a selected period of time.

Another embodiment of the UV-C light apparatus has a UV-C lamp combined with a quarter wave transformer to generate UV-C light having a light spectrum between 200 nm and 230 nm. The UV-C light spectrum generated by the UV-C lamp can be limited to 222±1 nm. A housing has a chamber and an opening to the chamber. The UV-C lamp in the chamber emits UV-C light which is directed from the housing to a desired location to destroy pathogens. The housing has an upwardly and rearwardly inclined top wall for accommodating visual data regarding instructions for use of the apparatus and identity of the apparatus. The housing includes side walls joined to the top wall surrounding the chamber. The inside surfaces of the side walls and top wall are polished metal that function to reflect UV-C light to the desired location. A support is connected to at least one of the side walls to retain the housing in a selected location. The UV-C light apparatus employs a method of disinfecting and destroying pathogens with UV-C light having a spectrum between 207 nm and 222±1 nm. The light spectrum can be expanded to 200 nm to 230 nm. The UV-C light spectrum is not extended beyond 230 nm. The UV-C light is produced with a UV-C light source, such as a UV-C lamp or UV-C light diodes operably coupled to a quarter wave transformer.

DESCRIPTION OF THE FAR UV-C LIGHT APPARATUS

The Far UV-C light apparatus 10, illustrated in FIGS. 1 to 7, generates a far UV-C light spectrum between 207 nm and 222±1 nm for use as a germicidal light. The UV-C light spectrum can be expanded to 200 nm to 230 nm. The optimum UV-C light wavelength is 222±1 nm The apparatus 10 does not generate a UV-C light spectrum in excess of 230 nm. The generated UV-C light spectrum may be less than 207 nm, including 200 nm. The UV-C light apparatus 10 incorporates quarter wave technology to generate the far UV-C light spectrum between 207 nm and 222±1 nm.

Figure 1:
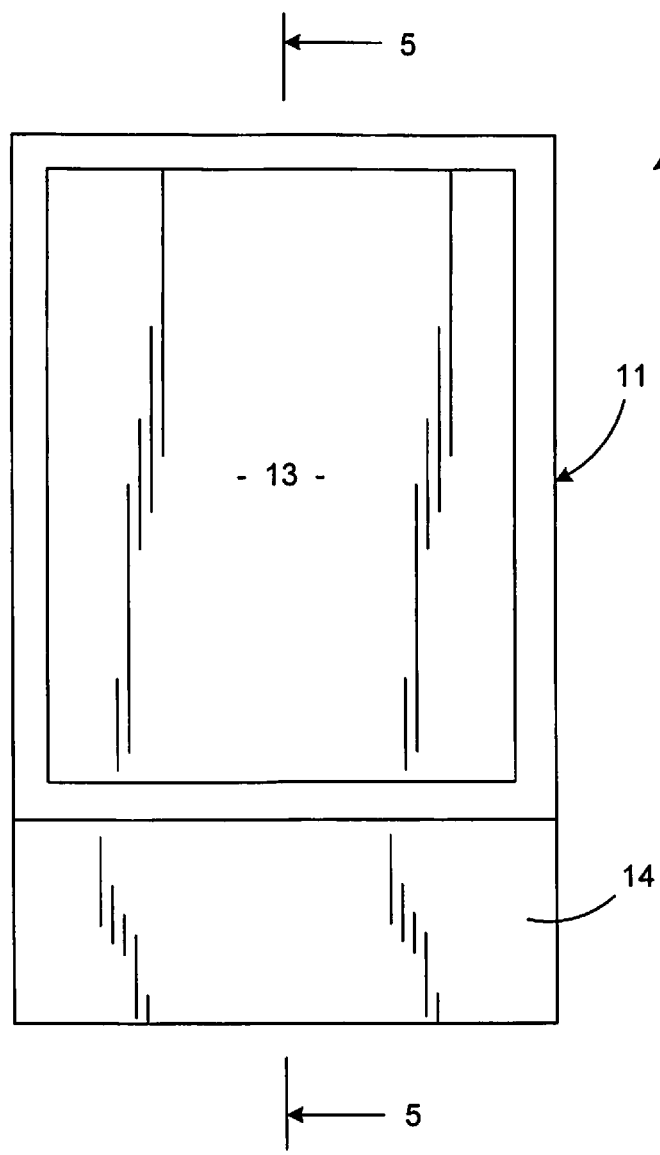
FIG. 1 is a front elevational view of a first embodiment of the Far UV-C light apparatus of the invention.
Figure 2:
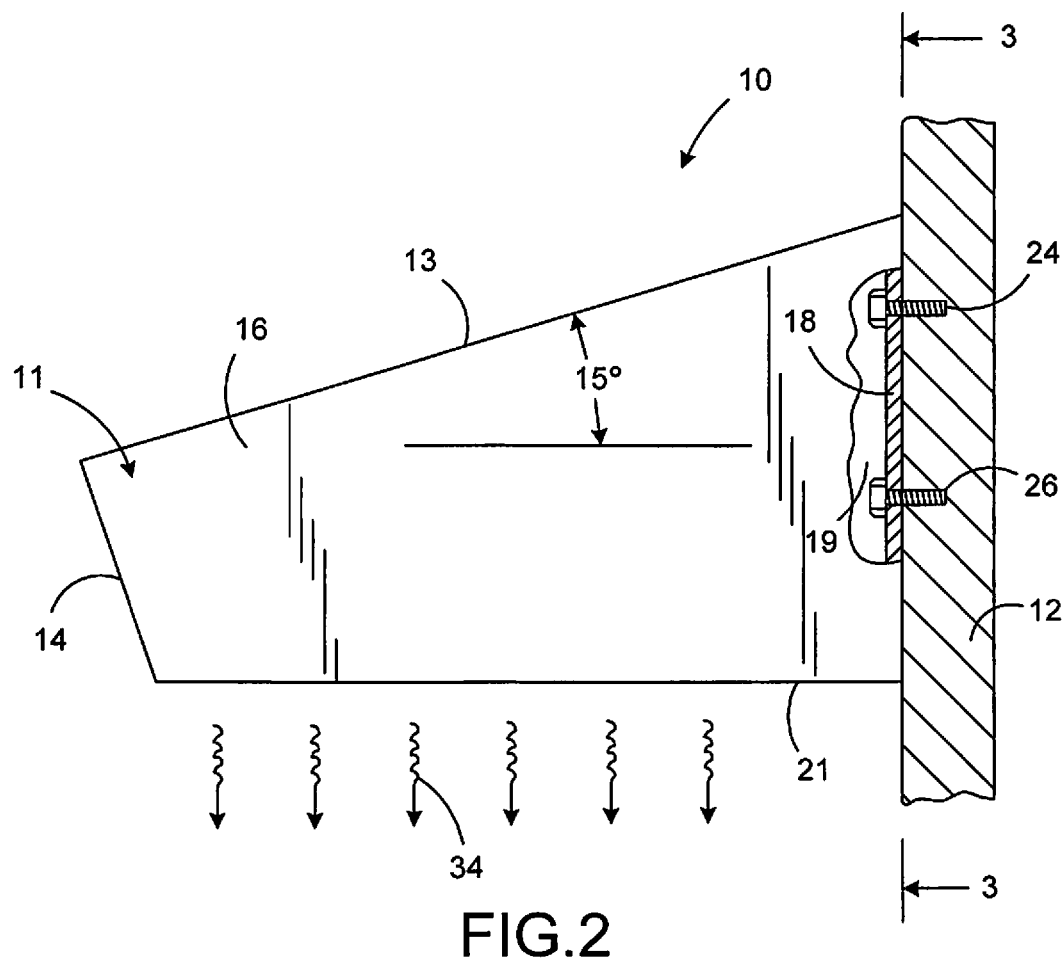
FIG. 2 is a right side elevational view, partly sectioned, of FIG. 1 mounted on a vertical support.

The UV-C light apparatus 10 has a housing 11 surrounding a UV-C light source, shown as a UV-C lamp or bulb 33, that functions to emit or generate a UV-C light spectrum between 207 nm and 222±1 nm, shown by arrows 34. Housing 11, shown in FIG. 2, is mounted on an upright support 12, shown as a building wall 12. Other types of supports, including doors, posts, carts and movable structures, can be used to hold housing 11 in a selected location. Housing 11 has a top wall 13 joined to a front wall 14, side walls 16 and 17 and a back wall 18. The walls 14 and 16 to 18 extend downward from top wall 13 and surround a chamber 19 accommodating a UV-C lamp 33. Housing 11 has a bottom opening 21. Walls 13, 14 and 16 to 18 are sheet metal members having polished inside surfaces that reflect UV-C light toward bottom opening 21. Top wall 13, shown in FIG. 2, inclines upwardly and rearwardly at an angle of 15 degrees relative to the horizontal plane of the bottom edges of walls 14 and 16 to 18. Top wall 13 can be inclined upward in a rearward direction at other selected directions to provide a person with visual exposure to the top surface of top wall 13 and identification and information data concerning the source and the use of the UV-C light apparatus 10.

Figure 3:
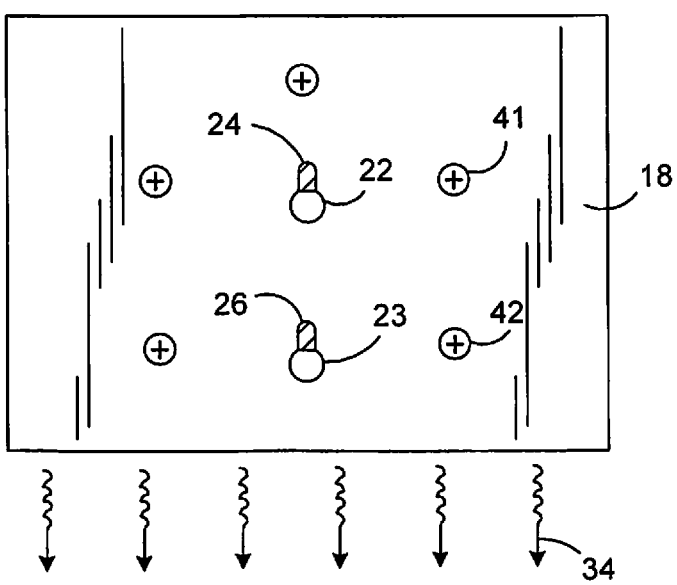
FIG. 3 is a sectional view taken along the line 3-3 of FIG. 2.

As shown in FIGS. 2 and 3, back wall 18 has a pair of keyhole slots 22 and 23. Fasteners 24 and 26 attached to support 12 have outer ends extended into keyhole slots 22 and 23 for mounting housing 11 on support 12. Other structures can be used to retain housing 11 on support 12. A handle 15, shown in FIG. 5, attached to wall 18 allows housing 11 to be hand held and manually moved relative to a selected location. Several handles can be attached to housing 11 to allow both hands of a person to move housing 11.

Figure 4:
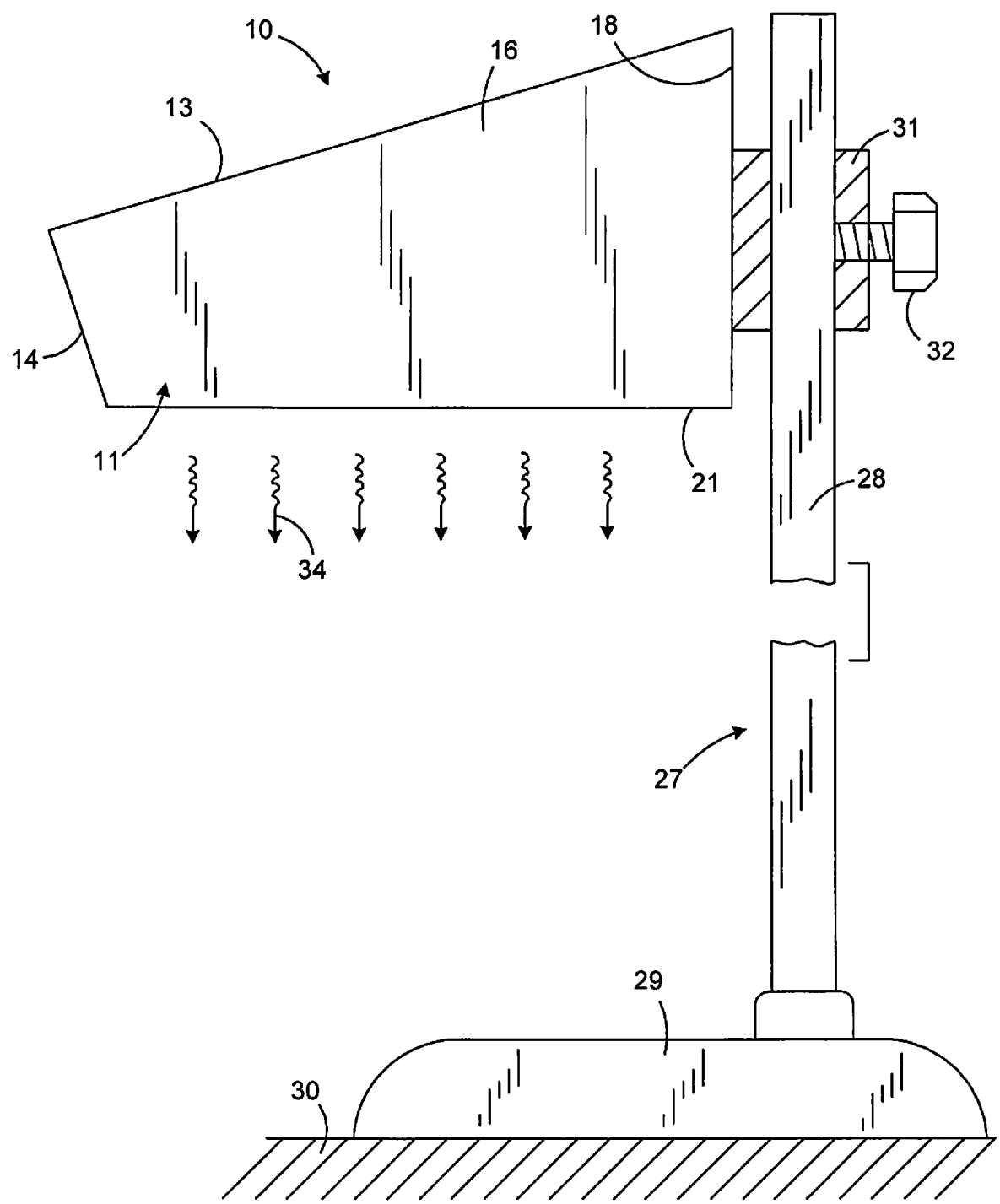
FIG. 4 is a right side elevational view of FIG. 1 mounted on a portable stand.

As shown in FIG. 4, housing 11 is mounted on a portable stand 27 to locate housing 11 above a floor 30. Stand 27 comprises an upright tubular post 28 secured to a semi-hemispherical base 29. Base 29 is supported on floor 30 or other types of horizontal surfaces. A sleeve 31 surrounding post 28 is connected to the back wall 18 of housing 11. Sleeve 31 horizontally supports housing 11 on post 28. A fastener 32, shown as a threaded bolt, threaded into sleeve 31 clamps sleeve 31 onto post 28. Fastener 32 allows the position of sleeve 31 and housing 11 to be vertically adjusted on post 28. Alternative fasteners can be used to secure housing 11 to post 28.

Figure 5:
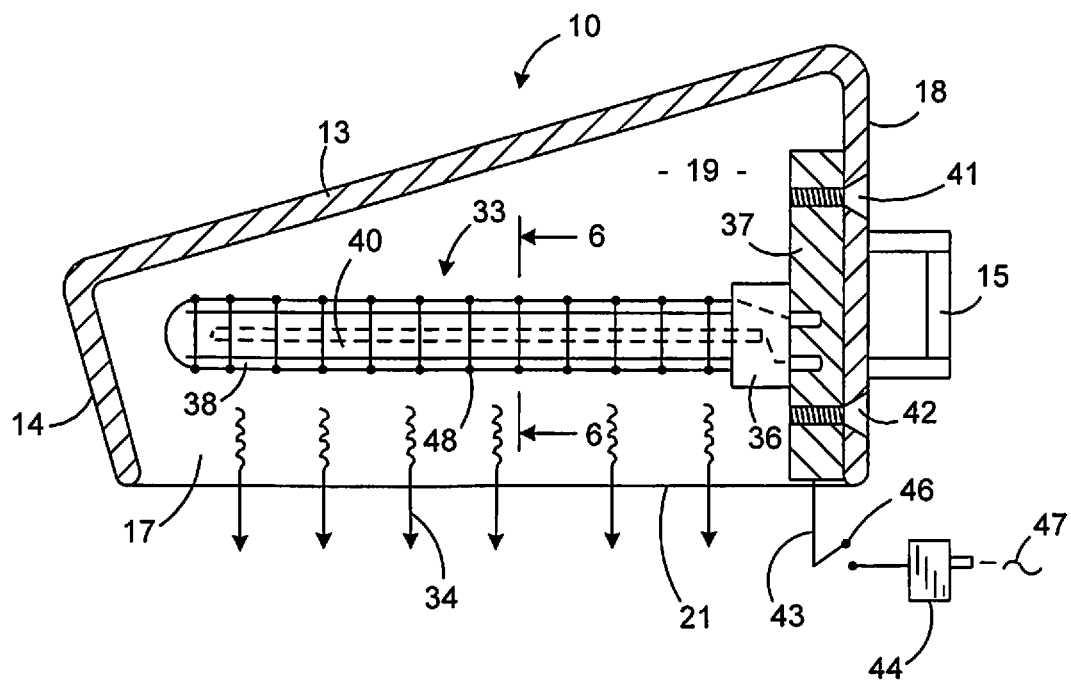
FIG. 5 is a sectional view taken along the line 5-5 of FIG. 1.
Figure 6:
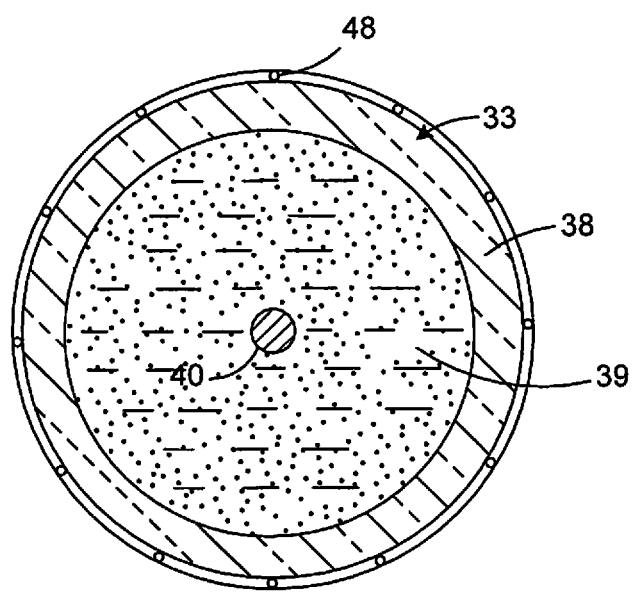
FIG. 6 is an enlarged sectional view taken along the line 6-6 of FIG. 5.
Figure 7:
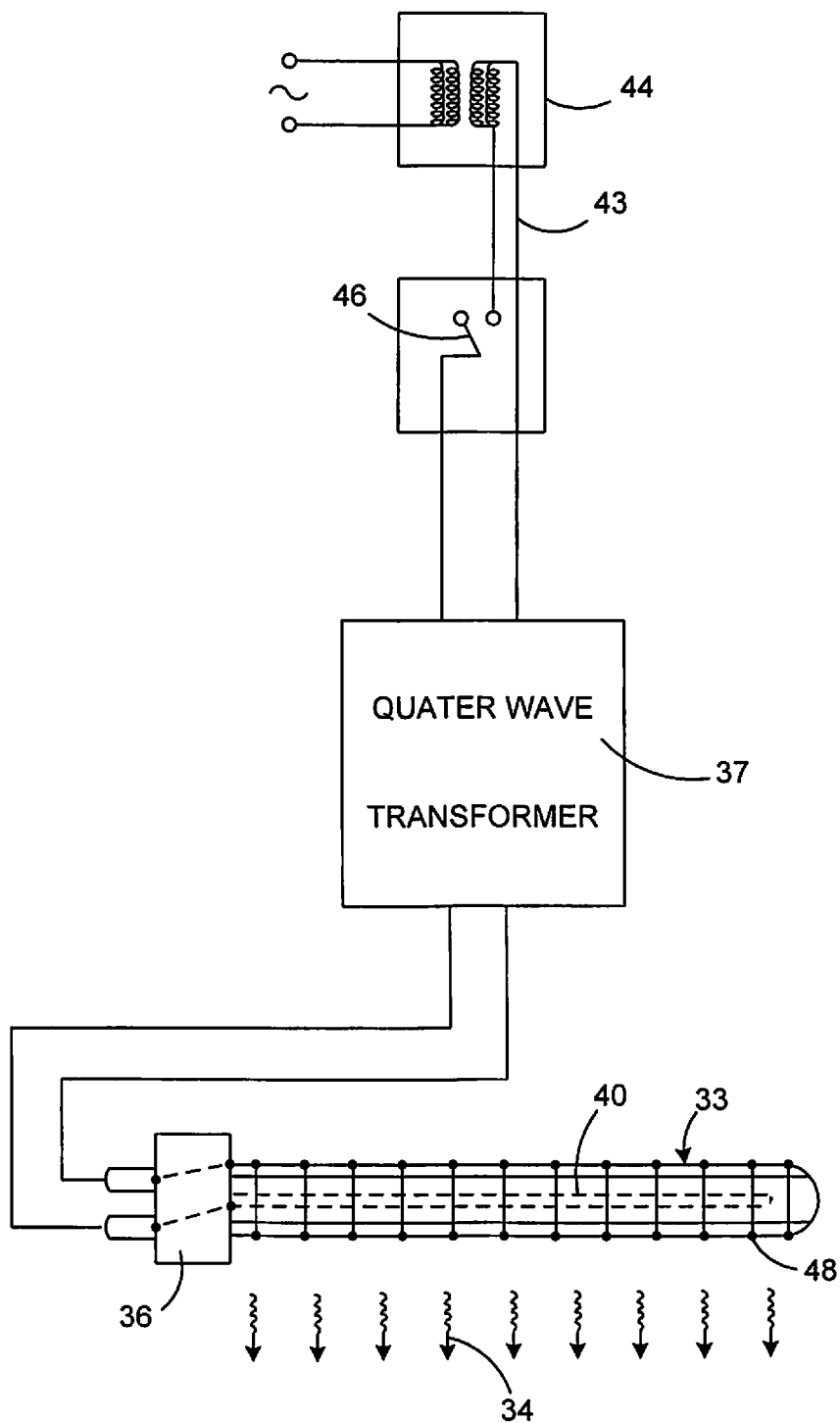
FIG. 7 is a diagram of the far UV-C light apparatus.
Figure 8:
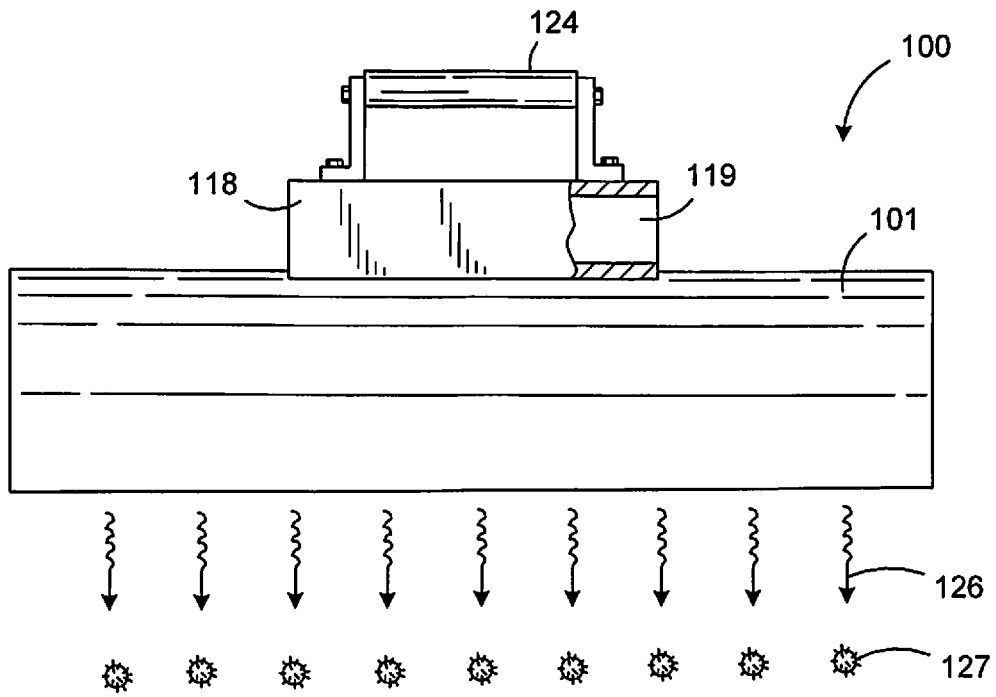
FIG. 8 is a front elevational view, partly sectioned, of a second embodiment of the Far UV-C light apparatus of the invention.
Figure 9:
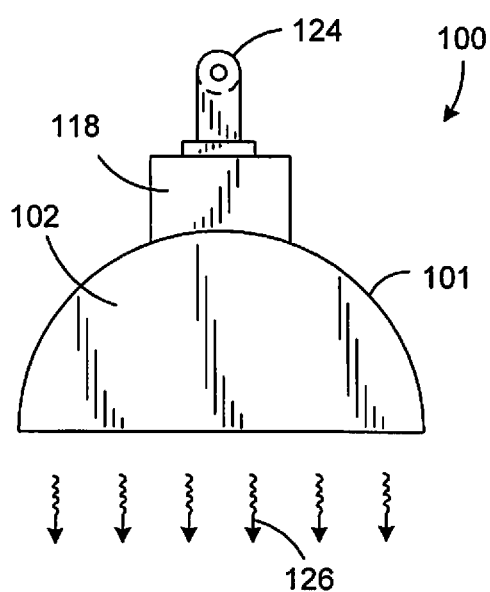
FIG. 9 is a right side elevational view of FIG. 8.
Figure 10:
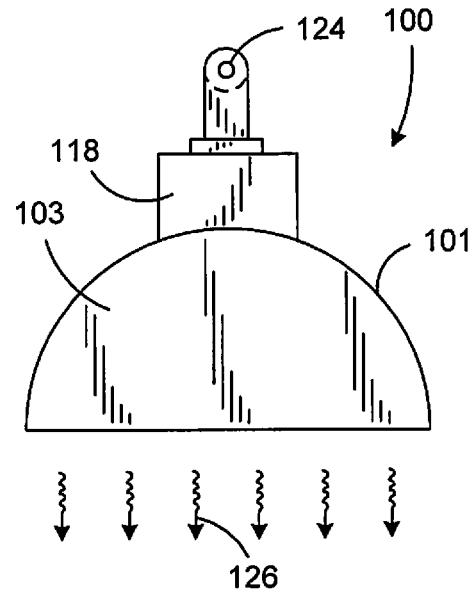
FIG. 10 is a left side elevational view of FIG. 8.
Figure 11:
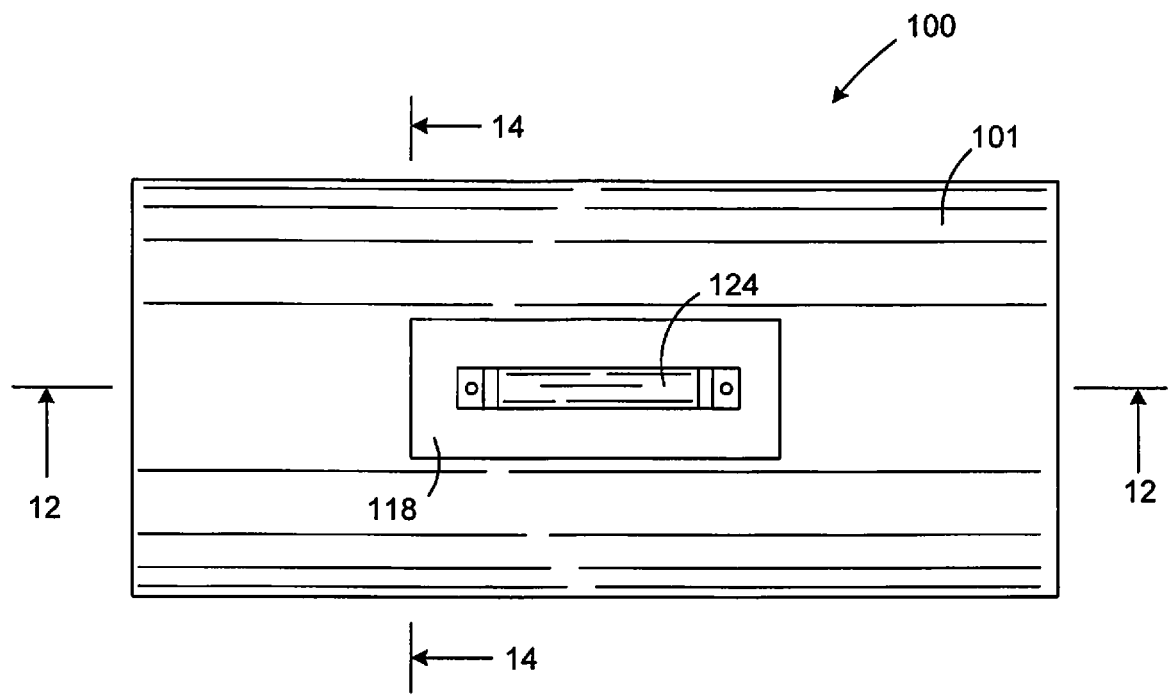
FIG. 11 is a top plan view of FIG. 8.

Proceeding to FIGS. 5 and 7, UV-C lamp 33 has an end base or connector 36 releasably joined to a quarter wave transformer 37. Fasteners 41 and 42 secure quarter wave transformer 37 to the inside of back walls 18 of housing 11. Quarter wave transformer 37 can be secured to the outside of back wall 18 or one of the side walls 16 and 17 of housing 11. UV-C lamp 33 is an elongated linear cylindrical tube 38 having a chamber 39 containing chemically inactive gases comprising a combination of argon and neon (Ar,Ne). Other chemically inactive gases can be used in the chamber 39 of tube 38. An electric conductor or wire 40 extended the length of the center of chamber 39 is wired to the electric circuit of quarter wave transformer 37. D.C. electric power, 15 volts, from a AC-DC transformer 44 is transmitted via electrical conductor or cable 43 to quarter wave transformer 37. An ON-OFF switch 46 interposed in cable 43 controls the D.C. electric power supplied to quarter wave transformer 37.

In an alternative apparatus, a number of light emitting diodes, LEDS, can be mounted within housing 11 to generate UV-C light having a light spectrum between 207 nm and 222±1 nm. The LEDS are electrically connected to the quarter wave transformer to control the UV-C light generated by the LEDS.

Quarter wave transformer 37 has a power inverter circuit having the function of inverting the impedance of the wire 40 in the UV-C lamp 33 to produce a desired impedance. The wire 40 is terminated at an impedance that is different from a characteristic impedance resulting in a wave being reflected from the termination back to the source. At the input to the wire 40 the reflected voltage adds to the incident voltage and the reflected current subtracts from the incident current. The section of wire 40 that is one quarter wavelength long at the fundamental frequency being transmitted, when shortened at the far end, has a high impedance at the functional frequency and all odd harmonics and a low impedance for all even harmonics. The result is a light spectrum of 207 nm to 222±1 nm radiating from UV-C lamp 33.

The apparatus 10 predicates a method of disinfecting and destroying pathogens on a surface, object or a person. The UV-C light is generated with a UV-C lamp 33 or UV-C diodes. The UV-C lamp 33 is operatively coupled to the quarter wave transformer 37 which controls the UV-C light spectrum of the UV-C lamp between 207 nm and 222±1 nm wavelengths. The UV-C light between 207 nm and 222±1 nm wavelengths is directed to the surface, object or person to disinfect pathogens. Alternatively, an air stream can be exposed to the UV-C light to destroy pathogens entrained in the air stream.

A second embodiment of the Far UV-C light apparatus, shown in FIGS. 8 to 14, is a hand held portable device 100 utilizing Far UV-C light 74 to neutralize and destroy pathogens including viruses, bacteria, spores and yeasts. Device 100 has a housing 101 accommodating a Far UV-C light source 108. Housing 101 comprises a semi-circular body 105 joined to end walls 102 and 103. Body 105 has a concave inside surface 104. Body 105 is an aluminum member with surface 104 being polished to reflect Far UV-C light. Body 105 and end walls 102 and 103 surround a chamber 106 having a bottom opening 107. A Far UV-C light source 108 located within chamber 106 emits Far UV-C light, illustrated by arrows 126, toward a location containing pathogens 127.

Figure 12:
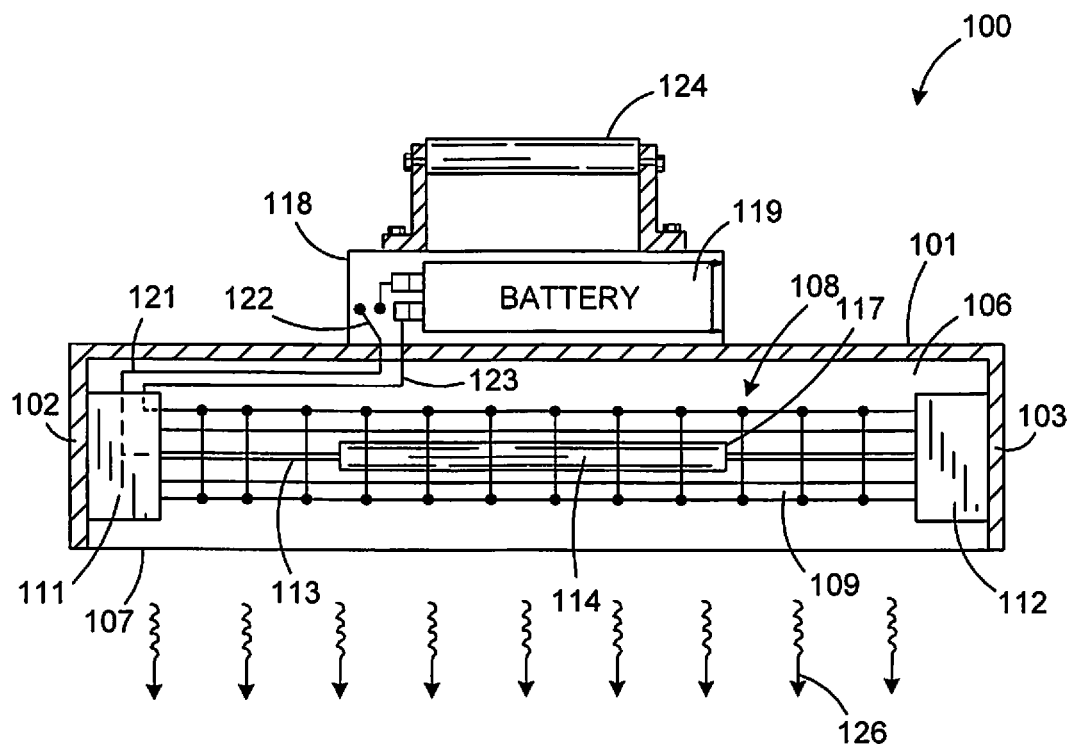
FIG. 12 is a sectional view taken along line 12-12 of FIG. 11.
Figure 13:
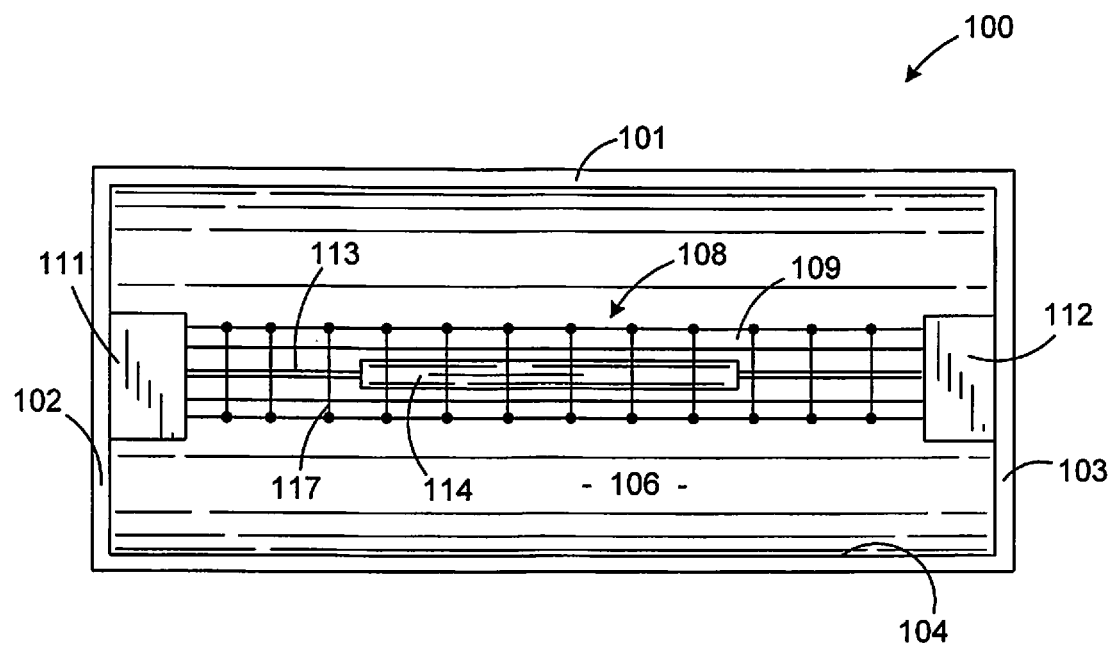
FIG. 13 is a bottom plan view of FIG. 8.
Figure 14:
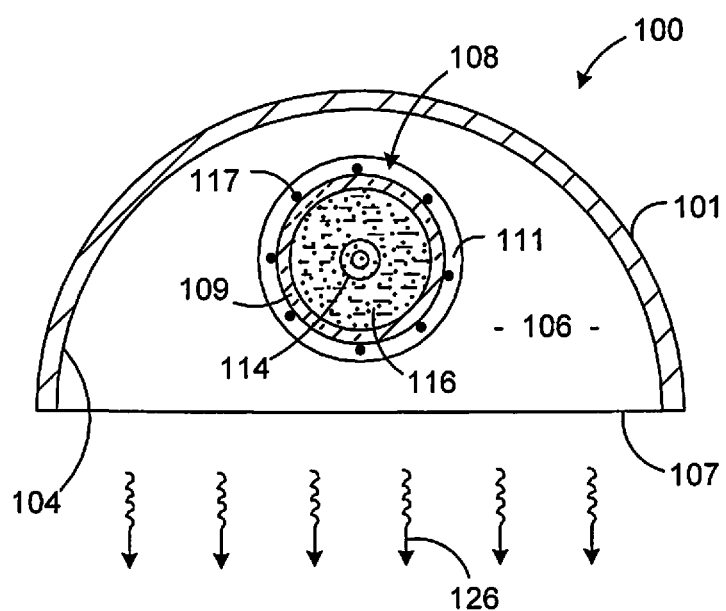
FIG. 14 is an enlarged sectional view taken along line 14-14 of FIG. 11.

Far UV-C light source 108, shown in FIGS. 12, 13 and 14, comprises an elongated cylindrical tubular lamp 109 attached to end members or caps 111 and 112. Lamp 109 can have an elongated square shape. The caps 111 and 112 are secured to end walls 102 and 103 to hold lamp 109 in chamber 106 parallel to the bottom opening 107. As shown in FIGS. 12, 13 and 14, a rod 113 supports a sleeve 114 in the chamber 116 of lamp 109. Rod 113 and sleeve 114 are metal electrical conductors. A wire mesh electrical conductor 117 is located around the outside surface of lamp 109. An inert gas, such as a mixture of krypton and chlorine gas, is sealed in the chamber 116 of lamp 109. The inert gas when subjected to electric energy emits Far UV-C light having a wavelength of 222±1 nm.

A casing or holder 118 for a battery 119 is attached to housing 101. Battery 119 is wired to rod 113 and wire mesh 117 with electric conductor or wires 121 and 123. A ON-OFF switch 122 associated with electric conductor 121 is manually operated to electrically connect battery 119 to lamp 109. A motion sensor switch 122 for actuating the electric circuit associated with the electric conductor 121 automatically connects battery 119 to lamp 109. An example of a motion sensor for turning off a UV-C lamp is disclosed in U.S. Patent Application Publication No. US2016/0339133. Battery 119 can be removed from casing 118 and recharged. An A.C. to D.C. transformer can replace battery 119 to permit A.C. electric supply to activate lamp 109.

A handle 124 attached to casing 118 allows a person to manually hold and move housing 101 to selected locations to sanitize the selected locations. One or more handles can be attached to housing 101 to facilitate manual movement of the housing 101.

There has been disclosed several embodiments of the apparatus and method of generating germicidal light with a UV-C lamp coupled to a quarter wave transformer. Variations of the structure and use of the apparatus can be made by a person skilled in the art without departing from the invention. For example, the UV-C lamp can be incorporated in a hand held housing, a movable cart, a person's hat or cap, a table or the ceiling or wall of a structure.

The invention claimed is:

1. An apparatus for sterilizing pathogens with UV-C light comprising:

a UV-C light source for emitting UV-C light having a light spectrum between 207 nm and 230 nm, a quarter wave generator operably connected to the UV-C light source for supplying electric energy to the UV-C light source whereby the UV-C lamp produces UV-C light having a light spectrum between 207 nm and 230 nm, and a D.C. transformer connected to an electric power source operable to supply D.C. electric energy to the quarter wave generator.

2. The apparatus of claim 1 including:

a housing having a chamber accommodating the UV-C light source, said housing having an opening to the chamber whereby the UV-C light from the UV-C light source is directed to a location having pathogens.

3. The apparatus of claim 2 wherein:

the housing includes a top wall inclined in a rearward and upward direction, said top wall having a surface for supporting visual information concerning the apparatus.

4. The apparatus of claim 2 including:

an upright support secured to the housing, and a base secured to the upright support for maintaining the upright support in an upright position on a supporting surface.

5. The apparatus of claim 1 wherein:

the UV-C light source comprises a Far UV-C lamp.

6. The apparatus of claim 1 wherein:

the UV-C light source emits Far UV-C light having a light spectrum of 222±1 nm.

7. The apparatus of claim 1 including:

a housing having a chamber accommodating the UV-C light source, and a handle attached to the housing for manually holding and moving the housing to selected locations.

8. The apparatus of claim 1 including:

a motion sensor operable to turn on the electric energy to the generator in response to motion of an object detected by the motion sensor.

9. An apparatus for neutralizing pathogens comprising:

a housing having upright side walls, an upright front wall, an upright rear wall and a top wall joined to the side walls, the front wall and the rear wall, said top wall being inclined upwardly and rearwardly from the front wall toward the real wall, said top wall having a surface for accommodating visual information, said side walls, the front wall, the rear wall and the top wall surrounding a chamber having a bottom opening, an upright support having an upper section secured to one of the side walls of the housing, a base secured to the upright support for maintaining the upright support in an upright position on a supporting surface, a UV-C light source for producing UV-C light having a light spectrum of 222±1 nm, a D.C. transformer connected to an electric power source operable to supply electric energy to the UV-C light source whereby the UV-C light source emits UV-C light having a spectrum of 222±1 nm, and structure for attaching the UV-C light source to at least one of the side walls of the housing to locate the UV-C light source within the chamber of the housing whereby the UV-C light from the UV-C light source is directed from the chamber through the bottom opening to a selected location to neutralize pathogens in the selected location.

10. The apparatus of claim 9 wherein:
the UV-C light source comprises a Far UV-C lamp.

11. The apparatus of claim 9 including:
a motion sensor operable to turn on the electric energy to the D.C. transformer in response to motion of an object detected by the motion sensor.

12. The apparatus of claim 9 including:
at least one member securing the upper section of the support to the one of the side walls of the housing.

13. An apparatus for neutralizing pathogens comprising:
a body having a first end and a second end opposite the first end and a concave inside surface extended between the first end and the second end, a first end wall joined to the first end of the body and a second end wall joined to the second end of the body,
said concave inside surface, the first end wall and the second end wall surrounding a chamber having an opening,
a UV-C light source located in the chamber of the body operable to emit UV-C light having a light spectrum between 207 nm and 230 nm,
at least one member for supporting the UV-C light source on the body, and
an electric energy supply operatively connected to the UV-C light source for providing electric energy to the UV-C light source whereby the UV-C light source emits UV-C light through the opening to a selected location to neutralize pathogens in the selected location.

14. The apparatus of claim 13 wherein:
the concave inside surface of the body comprises a semi-cylindrical surface.

15. The apparatus of claim 13 wherein:
the concave inside surface of the body is a polished metal surface for reflecting UV-C light toward the opening of the chamber.

16. The apparatus of claim 13 wherein:
the UV-C light source comprises a Far UV-C light lamp.

17. The apparatus of claim 16 wherein:
the Far UV-C light lamp has a light spectrum of 222±1 nm.

18. The apparatus of claim 13 including:
a handle attached to the body for holding and moving the apparatus to selected locations.

19. The apparatus of claim 13 wherein:
the electric energy supply is a battery operatively connected to the UV-C light source.

20. The apparatus of claim 19 including:
a casing attached to the body,
said battery being located within the casing, and
a handle attached to the casing.

\* \* \* \* \*